(12) United States Patent
Desborough

(10) Patent No.: US 12,308,103 B2
(45) Date of Patent: May 20, 2025

(54) MINIMALLY BURDENSOME BLOOD GLUCOSE MANAGEMENT FOR INSULIN-REQUIRING DIABETES

(71) Applicant: Nudge BG, Inc., Thousand Oaks, CA (US)

(72) Inventor: Lane Desborough, Thousand Oaks, CA (US)

(73) Assignee: Nudge BG Inc., Thousand Oaks, CA (US)

( * ) Notice: Subject to any disclaimer, the term of this patent is extended or adjusted under 35 U.S.C. 154(b) by 911 days.

(21) Appl. No.: 17/149,611

(22) Filed: Jan. 14, 2021

(65) Prior Publication Data

US 2021/0220559 A1    Jul. 22, 2021

Related U.S. Application Data

(60) Provisional application No. 62/962,179, filed on Jan. 16, 2020, provisional application No. 62/962,178, filed on Jan. 16, 2020.

(51) Int. Cl.
| | |
|---|---|
| *G16H 20/17* | (2018.01) |
| *A61M 5/142* | (2006.01) |
| *A61M 5/172* | (2006.01) |
| *G05B 23/02* | (2006.01) |
| *G16H 40/40* | (2018.01) |
| *G16H 40/67* | (2018.01) |

(52) U.S. Cl.
CPC ........ *G16H 20/17* (2018.01); *A61M 5/14248* (2013.01); *A61M 5/1723* (2013.01); *G05B 23/0272* (2013.01); *G16H 40/40* (2018.01); *G16H 40/67* (2018.01); *A61M 2205/18* (2013.01); *A61M 2205/3584* (2013.01); *A61M 2205/502* (2013.01); *A61M 2230/201* (2013.01)

(58) Field of Classification Search
None
See application file for complete search history.

(56) References Cited

U.S. PATENT DOCUMENTS

| | | |
|---|---|---|
| 9,878,097 B2 | 1/2018 | Estes |
| 11,101,030 B2 | 8/2021 | Desborough |
| 11,942,202 B2* | 3/2024 | Desborough .......... G16H 20/17 |
| 2008/0021666 A1 | 1/2008 | Goode, Jr. et al. |

(Continued)

OTHER PUBLICATIONS

Notice of Allowance in U.S. Appl. No. 17/403,518 dated Dec. 20, 2023, 9 pages.

(Continued)

*Primary Examiner* — Manuel A Mendez

(57) ABSTRACT

Some embodiments include burden-free insulin delivery systems and methods. In some embodiments, a method may include receiving previous insulin delivery data at a user device from an insulin pump; receiving estimated glucose data at the user device from a continuous glucose monitor; determining an insulin delivery amount based on the previous insulin delivery data and the estimated glucose data to bring the estimated glucose data closer to a target glucose value without using any user-specific behavioral data physically entered by a user through a user interface of the user device within a previous period of time, the previous period of time being less than six hours; and communicating the insulin delivery amount to the insulin pump.

20 Claims, 7 Drawing Sheets

(56) References Cited

U.S. PATENT DOCUMENTS

| | | |
|---|---|---|
| 2009/0006034 A1 | 1/2009 | Hayter et al. |
| 2011/0184267 A1 | 7/2011 | Duke et al. |
| 2012/0226259 A1 | 9/2012 | Yodfat et al. |
| 2017/0086756 A1 | 3/2017 | Harper et al. |
| 2017/0189614 A1 | 7/2017 | Mazlish et al. |
| 2017/0203036 A1 | 7/2017 | Mazlish et al. |

OTHER PUBLICATIONS

Non-Final Office Action in U.S. Appl. No. 17/736,813 dated Aug. 8, 2024, 9 pages.
Non-Final Office Action in U.S. Appl. No. 17/736,825 dated Aug. 13, 2024, 11 pages.
Invitation to Pay Additional Fees as issued in connection with International Patent Application No. PCT/US2021/013496, mailed Mar. 9, 2021, 2 pages.
Non-Final Office Action in U.S. Appl. No. 17/149,598 dated Mar. 30, 2021, 10 pages.
International Search Report and Written Opinion as issued in connection with International Patent Application No. PCT/US2021/013496, mailed May 13, 2021, 11 pages.
Notice of Allowance in U.S. Appl. No. 17/149,598 dated May 25, 2021, 9 pages.
International Preliminary Report on Patentability as issued in connection with International Patent Application No. PCT/US2021/013496, mailed Jul. 19, 2022, 7 pages.
Non-Final Office Action in U.S. Appl. No. 17/403,518 dated Sep. 8, 2023, 18 pages.

\* cited by examiner

MINIMALLY BURDENSOME BLOOD GLUCOSE MANAGEMENT FOR INSULIN-REQUIRING DIABETES

BACKGROUND

Diabetes mellitus is a chronic metabolic disorder caused by an inability of a person's pancreas to produce sufficient amounts of the hormone, insulin, such that the person's metabolism is unable to provide for the proper metabolism of sugar and starch. The absence of endogenous insulin production can lead to 1) ketoacidosis, i.e. a buildup of acids in the bloodstream caused when the body breaks down fat as fuel in the absence of insulin, and 2) hyperglycemia, i.e. the presence of an excessive amount of glucose within the blood. Persistent hyperglycemia has been associated with a variety of serious symptoms and life threatening long-term complications such as dehydration, cardiovascular diseases, chronic renal failure, retinal damage and nerve damages with the risk of amputation of extremities. Because restoration of endogenous insulin production is not yet possible, therapies that provide glycemic control can be used to maintain the level of blood glucose within safe limits. Such glycemic control may be achieved by regularly supplying external drugs or hormones to the body of the person with diabetes to reduce the elevated levels of blood glucose.

Diabetes is often treated with multiple, daily injections of rapid and long acting insulin via a hypodermic syringe or insulin pen. One or two injections per day of a long acting insulin may be administered to provide a basal level of insulin and additional bolus injections of a rapidly acting insulin may be administered before or with each meal in an amount proportional to the size of the meal, or at time to correct a high blood glucose level and bring the person with diabetes' blood glucose back into a safe range. Insulin can also be administered using an insulin pump that provides periodic or continuous release of insulin to provide for a basal level of insulin and larger doses of that same insulin at the time of meals or when corrections are necessary.

People with diabetes, their caregivers, and their health care providers (HCPs) bear a great deal of cognitive burden in managing intensive medicine therapy. Delivering the correct amount of the medicine at the correct time is an extremely challenging endeavor. Such delivery requires the user—or their caregiver(s)—to make dosing determinations multiple times per day and also requires a combination of the person with diabetes and the HCP to recalibrate the therapeutic parameters of the therapy on an episodic time frame that varies from individual to individual, and within individuals based on age and/or behavior (e.g., change in exercise, change in diet, pregnancy, puberty).

SUMMARY

Some embodiments include a method comprising: receiving previous insulin delivery data from an insulin pump; receiving estimated glucose data from a continuous glucose monitor, determining an insulin delivery amount based on the previous insulin delivery data and the estimated glucose data to bring the estimated glucose data closer to a target glucose value without using any user-specific behavioral data physically entered by a user through a user interface of a device within a previous period of time, the previous period of time being less than 6 hours; and communicating the insulin delivery amount to the insulin pump.

In some embodiments, the previous insulin delivery data includes the amount of insulin delivered to the user over a period of time. In some embodiments, the period of time is between 2 and 15 minutes.

In some embodiments, the insulin delivery data is received from the insulin pump via Bluetooth. In some embodiments, the estimated glucose data is received from the continuous glucose monitor via Bluetooth.

In some embodiments, the user-specific behavioral data comprises data selected from the list consisting of one or more of a mealtime announcement, a meal carbohydrate content estimate, an exercise announcement, and a sleep announcement.

In some embodiments, the previous period of time comprises 3 hours. In some embodiments, the previous period of time comprises 1 hour. In some embodiments, the insulin delivery amount comprises an insulin correction to a basal insulin rate.

Some embodiments include a method comprising: receiving previous insulin delivery data from an insulin pump; receiving estimated glucose data from a continuous glucose monitor; determining an insulin delivery amount based on the previous insulin delivery data and the estimated glucose data to bring the estimated glucose data closer to a target glucose value without using user-specific physiological data that is physically entered by a user through a user interface of a device within the previous period of time, the previous period of time being less than 6 hours; and communicating the insulin delivery amount to the insulin pump.

In some embodiments, the previous insulin delivery data includes the amount of insulin delivered to the user over a period of time. In some embodiments, the period of time is between 2 and 15 minutes.

In some embodiments, the insulin delivery data is received from the insulin pump via Bluetooth. In some embodiments, the estimated glucose data is received from the continuous glucose monitor via Bluetooth.

In some embodiments, the user-specific behavior data comprises data selected from the list consisting of one or more of a mealtime announcement, a meal carbohydrate content estimate, an exercise announcement, and a sleep announcement.

In some embodiments, the previous period of time comprises 3 hours. In some embodiments, the previous period of time comprises 1 hour. In some embodiments, the insulin delivery amount comprises an insulin correction to a basal insulin rate.

Some embodiments include glucose management system comprising: a glucose monitoring device; an insulin pump; a user interface; and a controller in communication with the glucose monitoring device, the insulin pump, and the user interface, the controller receives previous insulin delivery data from the insulin pump, the controller receives estimated glucose data from the glucose monitoring device, the controller determines an insulin delivery amount based on the previous insulin delivery data and the estimated glucose data to bring an estimated glucose data closer to a target glucose value without using user-specific data that is physically entered by a user through the user interface within the previous period of time, the previous period of time being less than 6 hours, and the controller communicates the insulin delivery amount to the insulin pump.

In some embodiments, the glucose monitoring device and the insulin pump communicate wirelessly with the controller. In some embodiments, the glucose monitoring device is a class II insulin pump. In some embodiments, the glucose monitoring device is a class II integrated continuous glucose monitoring system. In some embodiments, the controller comprises a mobile device.

In some embodiments, the user-specific data comprises user-specific behavioral data or user specific physiological data. In some embodiments, the user-specific data comprises data selected from the list consisting of one or more of a mealtime announcement, a meal carbohydrate content estimate, an exercise announcement, and a sleep announcement. In some embodiments, the user-specific data comprises data selected from the list consisting of one or more of a glucose value, an estimated glucose value, a ketone measurement, an insulin delivery trend, physical activity data, movement data, and exertion data.

In some embodiments, the previous period of time comprises 3 hours. In some embodiments, the previous period of time comprises 1 hour.

In some embodiments, the controller wirelessly connects with either or both the glucose monitoring device or the insulin pump; the controller determines connectivity information regarding the connection between either or both the glucose monitoring device or the insulin pump; and the controller instructs the user interface to output connectivity information.

In some embodiments, the controller determines a fault in the glucose management system; and the controller instructs the user interface to output a fault indication.

In some embodiments, the fault comprises a fault selected from the list consisting of a glucose monitoring device end-of-life fault, a transient fault, a permanent fault, a battery end-of-life fault, a pump fault, an occlusion, a glucose sensor pull-out fault, a controller fault, and a system operation fault.

In some embodiments, the insulin delivery amount comprises an insulin correction to a basal insulin rate.

Some embodiments include a non-transitory computer-readable medium storing instructions that, when executed by a computing device, cause the computing device to: receive previous insulin delivery data from an insulin pump; receive estimated glucose data from a continuous glucose monitor; determine an insulin delivery amount based on the previous insulin delivery data and the estimated glucose data to bring the estimated glucose data closer to a target glucose value without using user-specific data that is physically entered by a user through a user interface of a device within the previous period of time, the previous period of time being less than 6 hours; and communicate the insulin delivery amount to the insulin pump.

In some embodiments, the user-specific data comprises user-specific behavioral data or user specific physiological data. In some embodiments, the user-specific data comprises data selected from the list consisting of one or more of a mealtime announcement, a meal carbohydrate content estimate, an exercise announcement, and a sleep announcement. In some embodiments, the user-specific data comprises data selected from the list consisting of a glucose value, an estimated glucose value, a ketone measurement, an insulin delivery trend, physical activity data, movement data, and exertion data.

In some embodiments, the previous period of time comprises 3 hours. In some embodiments, the previous period of time comprises 1 hour. In some embodiments, the insulin delivery amount comprises an insulin correction to a basal insulin rate.

Some embodiments include a method comprising: receiving previous insulin delivery data from an insulin pump; receiving estimated glucose data from a continuous glucose monitor; determining that the estimated glucose value is approaching or has passed a threshold; and in response to determining that the estimated glucose value is approaching or has surpassed the threshold, not providing an indication to the user through a user interface that the estimated glucose value is approaching or surpassed the threshold.

The method may also include determining an insulin delivery amount based on the previous insulin delivery data and the estimated glucose data to bring the estimated glucose data closer to a target glucose value without using any user-specific behavioral data physically entered by a user through a user interface of a device within a previous period of time, the previous period of time is less than 6 hours; and communicating the insulin delivery amount to the insulin pump.

In some embodiments, the indication is an alarm. In some embodiments, the indication is an alert.

In some embodiments, the user interface is part of a mobile device.

The method may also include determining an insulin delivery amount and communicating the insulin delivery amount to the insulin pump.

The method may also include determining an insulin delivery amount and delivering the insulin delivery amount to a user.

Some embodiments include a method comprising: receiving previous insulin delivery data from an insulin pump; receiving estimated glucose data from a continuous glucose monitor; and not providing data representative of the estimated glucose data or the insulin delivery data to a user through a user interface.

The method may also include determining an insulin delivery amount based on the previous insulin delivery data and the estimated glucose data to bring the estimated glucose data closer to a target glucose value without using any user-specific behavioral data physically entered by a user through a user interface of a device within a previous period of time, the previous period of time is less than 6 hours; and communicating the insulin delivery amount to the insulin pump.

In some embodiments, the data representative of the estimated glucose data comprises a value. In some embodiments, data representative of the estimated glucose data comprises a graph. In some embodiments, the data representative of the estimated glucose data comprises a trend line.

In some embodiments, the user interface is part of a mobile device or an insulin pump.

In some embodiments, the method may include an insulin delivery amount and communicating the insulin delivery amount to the insulin pump.

Some embodiments include a non-transitory computer-readable medium storing instructions that, when executed by a computing device, cause the computing device to: receive estimated glucose data from a continuous glucose monitor; determine that the estimated glucose value is approaching or has passed a threshold; and not provide an indication to the user through a user interface that the estimated glucose value is approaching or surpassed the threshold. The threshold, for example, may include a physiological threshold. The threshold, for example, may include a non-glucose related value.

In some embodiments, the non-transitory computer-readable medium further causes the computing device to: determine an insulin delivery amount based on the previous insulin delivery data and the estimated glucose data to bring the estimated glucose data closer to a target glucose value without using user-specific data that is physically entered by a user through a user interface of a device within the previous period of time, the previous period of time is less than 6 hours; and communicate the insulin delivery amount to the insulin pump.

In some embodiments, user-specific data may include any data manually or physically entered by a user. In some embodiments, user-specific data may include any data manually or physically into a user interface of a mobile device, insulin pump, or any connected device within a previous period of time such as, for example, more than 30, 60, 120, 240, 360, 480, etc. minutes.

In some embodiments, the indication is a textual or graphical representation of the trend or the pattern. In some embodiments, the indication is an alert or an alarm.

In some embodiments, the user interface is part of a mobile device or an insulin pump.

Some embodiments include a non-transitory computer-readable medium storing instructions that, when executed by a computing device, cause the computing device to: receive estimated glucose data from a continuous glucose monitor; determine that the estimated glucose value is approaching or has passed a threshold; and not provide data representative of the estimated glucose data or the insulin delivery data to a user through a user interface. The threshold, for example, may include a physiological threshold. The threshold, for example, may include a non-glucose related value. In some embodiments, if the threshold is not a physiological threshold or a non-glucose related threshold or may require some action on the part of the user, then an alert may be provided to the user.

In some embodiments, the non-transitory computer-readable medium further causes the computing device to: determine an insulin delivery amount based on the previous insulin delivery data and the estimated glucose data to bring the estimated glucose data closer to a target glucose value without using user-specific data that is physically entered by a user through a user interface of a device within the previous period of time, the previous period of time is less than 6 hours; and communicate the insulin delivery amount to the insulin pump In some embodiments, the data representative of the estimated glucose data comprises a textual value.

In some embodiments, the data representative of the estimated glucose data comprises a graph.

In some embodiments, the data representative of the estimated glucose data comprises a trend line.

In some embodiments, the user interface is part of a mobile device or an insulin pump.

Some embodiments include a method comprising: receiving previous insulin delivery data from an insulin pump; receiving estimated glucose data from a continuous glucose monitor; and in response to determining either or both the glucose trend or the glucose pattern, not displaying an indication of the trend or the pattern to a user.

In some embodiments, the method may also include determining an insulin delivery amount based on the previous insulin delivery data and the estimated glucose data to bring the estimated glucose data closer to a target glucose value without using any user-specific behavioral data physically entered by a user through a user interface of a device within a previous period of time, the previous period of time is less than 6 hours; and communicating the insulin delivery amount to the insulin pump.

In some embodiments, the either or both a glucose trend or a glucose pattern comprises a prediction of future estimated glucose in the user's blood. In some embodiments, the either or both a glucose trend or a glucose pattern comprises one of increasing glucose levels or decreasing glucose levels.

In some embodiments, the indication is a textual or graphical representation of the trend or the pattern. In some embodiments, the indication is an alert or an alarm.

In some embodiments, the user interface is part of a mobile device.

In some embodiments, the method may include determining an insulin delivery amount and communicating the insulin delivery amount to the insulin pump.

Some embodiments include a glucose management system comprising: a glucose monitoring device; an insulin pump; a user interface; and a controller in communication with the glucose monitoring device, the insulin pump, and the user interface. In some embodiments, the controller receives previous insulin delivery data from the insulin pump; receives estimated glucose data from the continuous glucose monitor; determines an insulin delivery amount based on the previous insulin delivery data and the estimated glucose data; communicates instructions to the insulin pump to deliver the insulin delivery amount; determines that the estimated glucose value is approaching or has passed a threshold; and in response to determining that the estimated glucose value is approaching or has surpassed the threshold, the controller does not provide an indication to the user through the user interface of the user device that the estimated glucose value is approaching or surpassed the threshold.

In some embodiments, determining an insulin delivery amount based on the previous insulin delivery data and the estimated glucose data includes determining the insulin delivery amount to bring the estimated glucose data closer to a target glucose value.

In some embodiments, determining an insulin delivery amount based on the previous insulin delivery data and estimated glucose data includes determining the insulin delivery amount without using any user-specific behavioral data physically entered by a user through a user interface of the user device within a previous period of time.

In some embodiments, the previous period of time is less than 6 hours. In some embodiments, the previous period of time is less than 120 minutes.

In some embodiments, the threshold comprises an estimated glucose value. In some embodiments, the indication is an alarm and/or an alert.

In some embodiments, the user interface is part of the user device. In some embodiments, the controller determines an insulin delivery amount and communicating the insulin delivery amount to the insulin pump.

The various embodiments described in the summary and this document are provided not to limit or define the disclosure or the scope of the claims.

BRIEF DESCRIPTION OF THE FIGURES

These and other features, aspects, and advantages of the present disclosure are better understood when the following Detailed Description is read with reference to the accompanying drawings.

DETAILED DESCRIPTION

Figure 1:
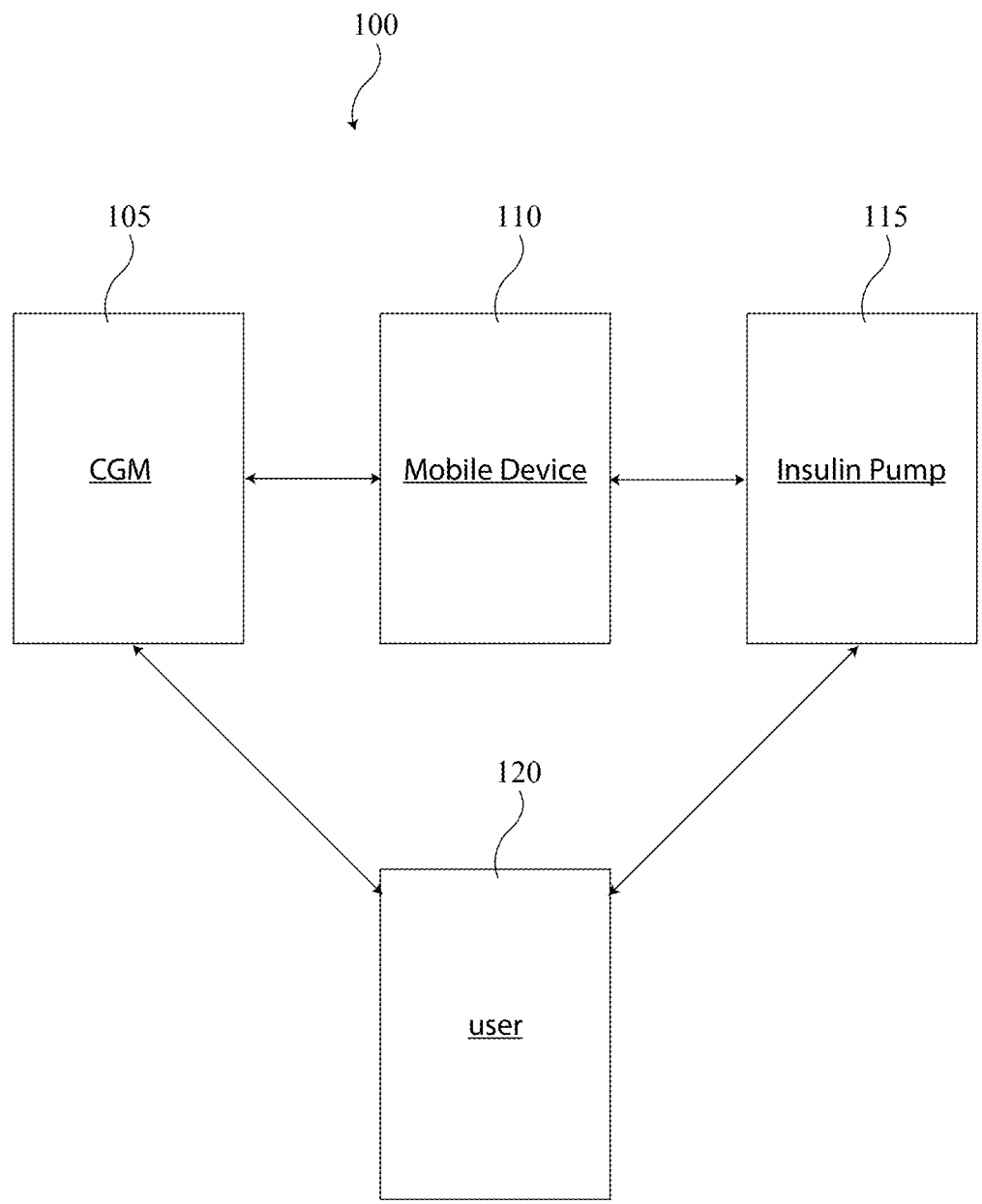
FIG. 1 is a block diagram of a glucose management system according to some embodiments.

Some embodiments include a burden-free glucose management system. A burden-free glucose management delivery system, for example, may not use or require user-specific physiological data and/or user-specific behavioral data to deliver insulin to the user. Neither the user nor the health care provider, for example, may be required to input user-specific physiological data and/or user-specific behavioral data into the system.

People living with insulin-requiring diabetes are responsible for making regular, consequential observations and decisions relating to glucose monitoring and insulin delivery. These people typically sense blood glucose and may manage many factors which might contribute to changes in their blood glucose. They often need to decide appropriate treatment interventions such as, for example, eating carbohydrates to raise glucose from hypoglycemia or injecting insulin to lower blood glucose from hyperglycemia.

These regular, consequential observations and/or decisions may result in cognitive and emotional burden. One such burden may include the monitoring of blood glucose using a blood glucose meter, flash glucose monitor, or continuous glucose monitor. These devices may produce alarms and/or alerts that may be a regular and/or frustrating negative reinforcement, which may impair sleep and/or create embarrassing or stressful social situations. Another burden may be the estimation of insulin dose to offset the effect of eating carbohydrates or reducing hyperglycemia. Meal bolusing may require the estimation of meal size "carb counting" as well as estimating other factors (e.g., insulin sensitivity factor, carbohydrate ratio, insulin action time, etc.), which may result, for example, in a user-provided amount of bolus insulin to deliver. Some activities may be so burdensome, for example, that the user ceases therapy, stops performing activities, or resorting to a less safe and effective modality.

Misuse may also cause problems. For example, typical insulin boluses may be large enough to have a significant glucose-lowering effect, hence their miscalculation or misadministration may have catastrophic acute or chronic complications. Bolus use errors are common and dangerous.

The burden of constantly monitoring physiological and/or behavioral outputs in order to deliver appropriate treatment interventions (e.g., insulin or carbs) to maintain blood glucose may be significant. In addition, in some cases, burdens may limit the safety, efficacy, and/or sustained use of prior art glucose management insulin delivery systems.

Burdens may include physically entering user-specific physiological data, physically entering user-specific behavioral data, displaying trends, displaying glucose data, displaying insulin data, displaying graphs, producing alerts, producing alarms, etc.

In addition to these and other burdens, the consequence of use errors in the provision of physiological and/or behavioral inputs can be significant. Slips, mistakes, or lapses in the estimation or provision of carbohydrate, blood glucose, or insulin data may result in miscalculation of treatment. Bolusing insulin, but forgetting to eat can result in severe hypoglycemia, coma, or death. Eating but forgetting to bolus insulin can result in prolonged hyperglycemia or chronic complications. Rage bolusing to lower high blood glucose may precipitate hypoglycemia, over-administration of rescue carbs, and/or attendant hyperglycemia.

User involvement—the sharing of physiological and user-specific behavioral data with the system—thus presents a double-edged sword with significant burden and strong asymmetries of risk (risk of hypoglycemia, hypoglycemia, and therapy cessation).

Some embodiments of a burden-free glucose management system may provide benefits to a user. For example, a user may not need to announce meals (e.g., time and/or carbohydrate content) and/or view or receive ongoing indications (e.g., alerts or alarms) about glucose values, etc. As another example, some embodiments of a burden-free glucose management system may decrease a user's cognitive and/or emotional burden. As another example, some embodiments of a burden-free glucose management system may decrease use errors (e.g., slips, mistakes, lapses) in the provision of physiologic or behavioral inputs, which may lessen insulin overdose or underdose caused by use errors. As another example, some embodiments of a burden-free glucose management system may obviate the need for user action (e.g., consuming carbohydrates to treat hypoglycemia, bolusing insulin to treat hyperglycemia, providing deliberately incorrect inputs to bolus calculations to increase aggressiveness of automated insulin delivery, etc.), which may lessen the effects of user-induced instability in insulin delivery. As another example, some embodiments of a burden-free glucose management system may not require users to provide user-specific physiological data or user-specific behavioral data to configure and adapt therapy, which may increase the number of health care providers who have the motivation and/or ability to support users. Some embodiments of a burden-free glucose management system remove these burdens among others, which may, for example, increase use, access, and/or effectiveness of a burden-free glucose management system.

Some embodiments include a glucose management system that determines an insulin delivery amount that is not based on manually entered user-specific physiological data and/or user-specific behavioral data. Some embodiments may include a glucose management system that does not determine an insulin delivery amount based on user-specific data (e.g., behavioral or physiological data) entered by a user in a preceding time period. The proceeding time period, for example, may be up to six hours. As another example, the proceeding time period may be up to one, two or three hours).

In some embodiments, the insulin delivery amount may comprise a basal delivery amount of insulin or an insulin correction (or adjustment) to basal insulin rate, which may, for example, be a positive or negative correction (or adjustment).

One benefit of a burden-free glucose-responsive insulin delivery system may be to reduce user burden, which may increase use, access, or effectiveness.

In some embodiments, user-specific data is not required to configure a glucose management system to determine insulin delivery values. For example, the glucose management system may safely learn the insulin sensitivity during operation based on sequences and patterns of insulin delivery and CGM glucose values. The glucose management system may use various algorithms to determine insulin delivery values such as, for example, closed-loop identification methods, injection of dither signals into the feedback path, or other control engineering methods for identifying system dynamics.

In some embodiments, user-specific data may include physiological data that may include one or more of the following: a glucose value (e.g., possibly read by a user from a blood glucose meter or by reading blood from a finger stick), an estimated glucose value from a continuous glucose monitor, a ketone measurement from a ketone monitor, an insulin delivery trend from an insulin pump, a physical activity measurement from a heart rate monitor, movement data from an accelerometer, exertion data from a galvanic skin response perspiration monitors, etc.

In some embodiments, user-specific data may include any data manually or physically entered by a user within a time period. The time period may be an amount of time greater than 30, 60, 120, 240, 360, 480, etc. minutes.

In some embodiments, user-specific data may include behavioral data that may include one or more of the following: an upcoming mealtime announcement, a carbohydrate content estimate, a fat content estimate, a protein content estimate, an upcoming exercise announcement, present illness information, medication intake, a driving announcement, etc. In some embodiments, user specific data may include any data regarding the user's current or expected activity or behavior that may impact insulin delivery or glucose levels.

A mealtime announcement, for example, may include any kind of input or indication from a user to a controller or a mobile device that the user is planning or expecting to eat a meal in the near future or that the user has recently eaten a meal. A carbohydrate content estimate, for example, may include any kind of input or indication from a user to a controller or a mobile device with an estimate on the quantity (e.g., grams, exchanges, etc.) and/or the type (e.g., fast or slow) of carbohydrates that are likely to be eaten in the near future or that have recently been eaten by a user. A protein content estimate, for example, may include any kind of input or indication from a user to a controller or a mobile device with an estimate on the amount of protein that is likely to be eaten in the near future or that has recently been eaten by a user. A fat content estimate, for example, may include any kind of input or indication from a user to a controller or a mobile device with an estimate on the amount of fat that is likely to be eaten in the near future or that has recently been eaten by a user. An exercise announcement, for example, may include any kind of input or indication from a user to a controller or a mobile device that the user is planning to or is expecting to exercise, or has recently exercised, including the amount, duration, intensity, and type (e.g., aerobic, anaerobic, practice, competition, work, labor, etc.) of exercise, and/or an insulin type (e.g., rapid acting insulin, ultra-rapid acting insulin, regular human insulin, concentrated insulin, co-formulated insulin etc.).

In some embodiments, a burden-free glucose management system may not display or present values, trends, or patterns of various parameters to a user such as, for example, on the display of a mobile device. These parameters may include, for example, estimated glucose values from a continuous glucose monitor, insulin delivery values from an insulin pump, bolus data, insulin delivery rates, insulin on board values, etc. The trends may include, for example, rates of changes of values, values relative to thresholds, etc.

In some embodiments, a burden-free glucose management system may not alert a user or trigger an alarm via a mobile device based on various triggers, thresholds, or trends unless, for example, the user's health is in danger, glucose levels are low, and/or an extended period of time has elapsed, such as, for example, more than two, four, or six hours. For example, rather than alert the user that glucose levels are reaching a threshold and burden the user such as, for example, when there is no action required on the user's part, the glucose management system may determine an insulin delivery amount that can counteract glucose trend toward the threshold.

In some embodiments, a burden-free glucose management system may not require a user to input physiological or behavior data. In some embodiments, a burden-free glucose management system may not alert a user regarding sensed physiological data (e.g., blood glucose or similar data) approaching, reaching, or passing a threshold value.

In some embodiments, a burden-free glucose management system may alert a user for physiological or behavior data once over a large period of time such as, for example, over the course of a week, a month, or a year. In some embodiments, a burden-free glucose management system may alert a user for physiological or behavior data at the first use, at the first use after calibration, at the first use after purchase, at the first use during start up, etc.

In some embodiments, a burden-free glucose management system may not alert a user about physiological data or in response to physiological data reaching, approaching, or passing a threshold value. Physiological data may include any or all of high glucose levels, low glucose levels, fast glucose rising or falling levels, slow glucose rising or falling levels, insulin basal rates, insulin bolus amounts, insulin basal amounts, etc. As another example, a burden-free glucose management system may not send the user glucose alerts. Glucose alerts may include continuous glucose monitor high alert, continuous glucose monitor low alert, continuous glucose monitor fixed low alert, continuous glucose monitor rise alert, continuous glucose monitor rapid rise alert, continuous glucose monitor fall alert, continuous glucose monitor rapid fall alert, etc.

In some embodiments, a burden-free glucose management system may not send the user insulin delivery alerts. Insulin delivery alerts may include basal rate required alert, max hourly bolus alert, max bolus alerts, max basal alerts, min basal alerts, etc.

In some embodiments, a burden-free glucose management system may alert a user for non-physiological data or in response to non-physiological data reaching, approaching, or passing a threshold value. Non-physiological data may include low insulin level data, whether the insulin pump is turned off or on, incomplete bolus data, temperature data, load sequence errors, insulin pump malfunctions, etc.

In some embodiments, a burden-free glucose management system may alert a user for a non-physiological alert which may or may not be received from an insulin pump. A non-physiological alert may, for example, include any or all of the following: low insulin alert, insulin pump auto-off alarm, incomplete bolus alert, incomplete temp rate alert, incomplete load sequence alerts, incomplete setting alert, connection error alert, pairing code timeout, power source alert, data error alert, resume pump alarm, empty cartridge alarm, cartridge error alarm, cartridge removal alarm, temperature alarm, occlusion alarms, screen on/quick bolus button alarm, altitude alarm, reset alarm.

In some embodiments, a burden-free glucose management system may alert a user during calibration of a continuous glucose monitor. A calibration alert may, for example, include any or all of the following: startup calibration alert, second startup calibration alert, calibration alert (e.g., 12 hour calibration alert), incomplete calibration, calibration timeout, wait calibration error alert (e.g., wait 15 minute calibration error alert), calibration required alert, etc.

In some embodiments, a burden-free glucose management system may alert a user regarding system errors. A system error may, for example, include any or all of the following: a repeated unknown sensor glucose reading, unknown sensor glucose reading, low battery levels, transmitter errors, failed sensor, insulin pump errors, continuous glucose monitor unavailable, and/or continuous glucose monitor system error, low power, failed sensor(s), insulin pump unavailable, continuous glucose monitor low power alert, insulin pump low power alert, software update alert, etc.

In some embodiments, a burden-free glucose management system may be turned off or turned on by a user. For example, when the burden-free glucose management system is turned on, the user may be alerted as noted the previous paragraphs such as, for example, for system errors, in response to non-behavioral data, and/or in responses to non-physiological data; and when the burden-free glucose management system is turned off, the user may be alerted for any and all the alerts noted above, other alerts, system errors, in response to physiological data, in response to non-physiological data, etc.

In some embodiments, a burden-free glucose management system may be in communication with a cloud system via a wireless transceiver. The cloud system, for example, may provide software updates, firmware updates, algorithm updates, threshold updates, physiological parameter updates, etc. In some embodiments, the cloud system may shutdown the operation of a burden-free glucose management system such as, for example, when it is determined that the burden-free glucose management system is miscalculating insulin delivery amounts, when a government agency mandates a shutdown, when it is determined that the burden-free glucose management system is unsafe for a user or a group of users, etc. A shutdown may include providing a notice to users through a user interface that the burden-free glucose management system will be stopping in a period of time.

FIG. 1 is a block diagram of a glucose management system 100 according to some embodiments. The glucose management system 100 may include a continuous glucose monitor (CGM) 105, a mobile device 110, and an insulin pump 115. The glucose management system 100 interacts with user 120. In some embodiments, the mobile device 110 and the insulin pump 115 are combined in a single device or unit. In some embodiments, the mobile device 110 and the insulin pump 115 are separate devices or units in communication with each other.

In some embodiments, the CGM 105 may include any type of CGM device.

In some embodiments, the CGM 105 may include an interoperable continuous glucose monitoring system (iCGM) that provides continuous glucose readings which are updated every 5 minutes without presenting glucose levels, trends, and/or alerts to the user view the mobile device 510.

In some embodiments, the CGM 105 may include a CGM sensor, a CGM transmitter, and/or a display device. The CGM 105 may provide, for example, alerts or alarms that warn the user of low, impending low, high, or impending high glucose levels, or glucose levels which are rapidly changing. Alternatively, neither the CGM 105 nor the mobile device 110 may provide alerts or alarms that warn the user of low, impending low, high, or impending high glucose levels, or glucose levels which are rapidly changing.

In some embodiments, the CGM sensor may include a sensor applicator, plastic base ("transmitter holder"), and/or a sensor probe. The applicator, for example, may be a single use, disposable unit that contains an introducer needle holding the sensor probe. The applicator, for example, may deploy the needle and/or insert the CGM sensor under the skin. The needle, for example, may be retracted back into the applicator after insertion. The sensor probe may continuously measure glucose concentration in interstitial fluid and can be worn for up to a number of days (e.g., 10 days).

The CGM sensor, for example, may be worn by the user 120 such as, for example, on the arm, or in the abdomen or buttock. The CGM sensor may, for example, include a calibration code that the user may enter via the user's mobile device that is wirelessly connected to the CGM 105 to initialize a new CGM sensor. The CGM sensor may, for example, be factory calibrated and may not require any calibration code to initialize a new CGM sensor.

In some embodiments, the CGM transmitter may include a miniature radio transmitter that communicates with the mobile device 110. In some embodiments, the radio transmitter may include data processing functionality. The CGM transmitter may include a wireless transceiver for communication with the mobile device 110. The CGM Transmitter may be coupled with the CGM sensor.

In some embodiments, the mobile device 110 may include any type of mobile device such as, for example, a mobile phone, smart phone, a watch, a tablet, a wearable controller, insulin pump, etc. The mobile device 110 may include all or some of the components of computational device 600 shown in FIG. 6. In some embodiments, the mobile device 110 may be an interoperable automated glycemic controller (IAGC) as defined by the FDA.

In some embodiments, the mobile device 110 may automatically calculate insulin doses based on inputs such as glucose parameters and past insulin doses, and to command the delivery of insulin doses using the connected insulin pump 115. In some embodiments, the mobile device 110 may reliably and/or securely communicate with the insulin pump 115 to allow insulin delivery messages or commands to be sent, received, executed, and/or confirmed. In some embodiments, the mobile device 110 may be used in conjunction with digitally connected devices for the purpose of maintaining glycemic control.

In some embodiments, the mobile device 110 may include a wireless transceiver such as, for example, a Bluetooth transceiver or a similar transceiver.

In some embodiments, the mobile device 110 may be a hand-held device that wirelessly receives glucose information from the CGM 105 on a fixed schedule (e.g., every five minutes). For example, the mobile device 110 may include a touchscreen display. As another example, the touchscreen display may or may not display glucose readings such as, for example, the current glucose reading and glucose trends to the user. As another example, the mobile device 110 may or may not alert the user when glucose levels are outside of a target zone or when other important system conditions occur. As another example, the mobile device 110 may or may not automatically display any glucose readings such as, for example, as charts, trends, numbers, data, alarms, announcements, alerts, etc. As another example, the mobile device 110 may or may not display glucose readings such as, for example, as charts, trends, numbers, data, alarms, announcements, alerts, etc. upon a request from the user through a user interface.

The insulin pump 115 may include any type of insulin pump known in the art. In some embodiments, the insulin pump 115 may include a patch pump. A patch pump, for example, may include a pump device that does not require any physiological or behavior inputs or outputs. A patch pump, for example, may include a pump device that does or does not include buttons.

In some embodiments, the insulin pump 115 may include a tethered pump. A tethered pump, for example, may deliver insulin to a user via an infusion set at different subcutaneous sites.

In some embodiments, the insulin pump 115 may include an intraperitoneal pump. An intraperitoneal pump, for example, may include a pump that delivers insulin intraperitoneally via infusion set or an insulin port.

In some embodiments, the insulin pump 115 may include a pump system as well as an embedded controller (e.g., rather than or in addition to the mobile device 110) that may include an embedded algorithm (e.g., a control algorithm such as algorithms described in this document). An insulin pump 115, for example, may communicate wirelessly with the mobile device 110 and/or the CGM.

In some embodiments, the insulin pump 115 may be an ambulatory, battery operated, and/or rate-programmable infusion pump designed for the subcutaneous delivery of insulin. In some embodiments, the insulin pump 115 may deliver insulin at set and/or variable rates. In some embodiments, the insulin pump 115 may include a disposable cartridge (or bag or reservoir) that is actuated (e.g., via a motor, MEMs, phase change, nitinol shape memory alloy (SMA) wire, etc.) to deliver insulin into subcutaneous tissue or through patch pump or other delivery mechanism. In some embodiments, the insulin pump 115 may include a pen cartridge.

In some embodiments, the insulin pump 115 may be partially or completely implanted under the skin of the user (e.g., intraperitoneal delivery).

In some embodiments, the insulin pump 115 may include a user-operated interface display.

The insulin pump 115 may include a number of components. For example, the insulin pump 115 may include an electronic microprocessor and/or software control system. As another example, the insulin pump 115 may include a wireless transceiver that may be used to communicate with the mobile device 110 or another device. As another example, the insulin pump 115 may include a motor and encoder. As another example, the insulin pump 115 may include a rack drive mechanism. As another example, the insulin pump 115 may include an audible speaker or a vibrator to provide alarms, alerts and reminders to the user.

As another example, the insulin pump 115 may include a touch screen display that has a capacitive touch panel that detects a finger touch. As another example, the insulin pump 115 may include one or more buttons. The button(s), for example, may be used to turn on the touch screen display so that the user can operate their pump. The button(s), for example, may also provide users with a quick bolus option, which may allow a user to program and deliver a bolus of insulin through a sequence of presses, without the use of the touch screen. The button(s), for example, may also provide users with an ability to acknowledge or suppress notifications, without the use of the touch screen or an app on a mobile device. In some embodiments, the insulin pump 115 may provide audio or vibratory feedback to the user to confirm delivery.

In some embodiments, the insulin pump 115 may not include a quick bolus option.

In some embodiments, the insulin pump 115 may not provide audio or vibratory feedback.

In some embodiments, the insulin pump 115 may include an electrically-isolated USB port located on one end of the pump, which may be covered by a protective rubber door. The USB port may, for example, be accessible to patients and when connected with a power supply may be used to charge an internal lithium polymer battery, upload data to a computer, or download firmware from a computer. In some embodiments, the insulin pump 115 may provide the user with an indication of the remaining battery power on the display and alerts when the battery power is low.

In some embodiments, the insulin pump 115 may include two or more microprocessors; one or two may control the pump functionality, and a third may control the wireless transceiver. The insulin pump 115 may be capable of sending and receiving data to and from other interoperable devices such as, for example, the mobile device 110.

In some embodiments, the insulin pump 115 may act on commands from the mobile device 110 to adjust insulin dosing. In some embodiments, the insulin pump 115 may receive and display alerts and alarms to users based on information received from other interoperable devices.

In some embodiments, the insulin pump 115 may include an insulin cartridge. The insulin cartridge, for example, may be designed to hold up to 3 mL, or 300 units of insulin such as, for example, U-100, U-200, or U-500 rapid acting insulin. As another example, the insulin cartridge may be a single use cartridge and may be replaced at least once every number days, depending on an individual's specific insulin usage or the indications for use of the insulin.

In some embodiments, the insulin pump 115 may include a fillable insulin reservoir. For example, the insulin fill port may include a septum on the cartridge head, through which the patient can fill the insulin reservoir.

In some embodiments, the insulin pump 115 may use pre-filled insulin cartridges from which insulin is delivered to the user.

In some embodiments, the insulin pump 115 may also include a tubing connector, a syringe, a fill needle, a power supply, and/or other components.

The insulin pump 115, for example, may deliver a fixed amount of insulin at varying time periods to deliver the required insulin. As another example, the insulin pump 115 may deliver varying amounts at fixed time intervals (e.g., every 5 minutes). As another example, the insulin pump may deliver multiples of a fixed amount (0.05U every second) in fixed time intervals (e.g., every 5 minutes).

In some embodiments, the mobile device 110 and the insulin pump 115 may be embedded together as a single device.

Figure 2:
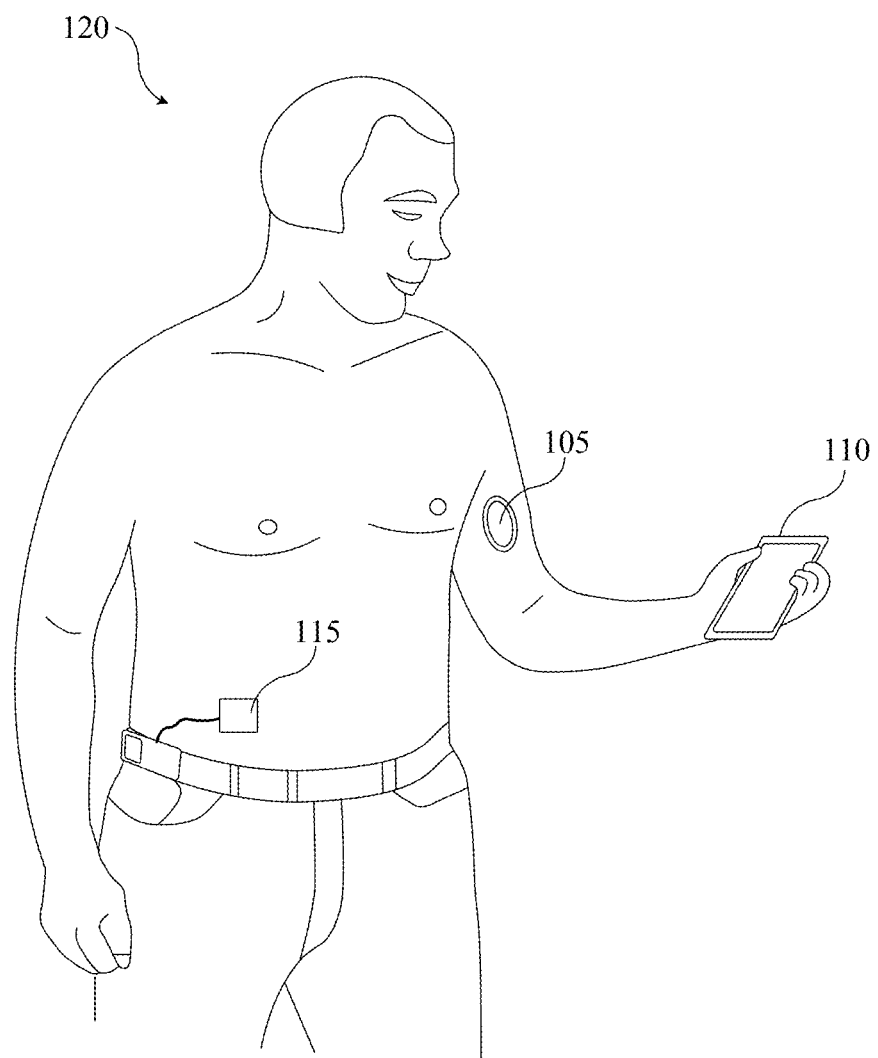
FIG. 2 is a diagram showing a glucose management system interacting with a user according to some embodiments.

FIG. 2 is a diagram showing the glucose management system 100 interacting with a user 120 according to some embodiments. In some embodiments, the CGM 105 may be attached to the user 120. The CGM sensor of the CGM 105 may measure or estimate the glucose level of the user and provide estimated glucose data to the mobile device 110. In some embodiments, the CGM 105 may wirelessly communicate the estimated glucose data. In some embodiments, the CGM 105 may send the estimated glucose data periodically such as, for example, every 1, 2, 5, 10, 15, etc. minutes. In some embodiments, the CGM 105 may be incorporated within a watch or another wearable device.

In some embodiments, the insulin pump 115 may be coupled with the user 120. The insulin pump 115 may provide previous insulin delivery data to the mobile device 110 via a wireless communication channel. The previous insulin delivery data may include data specifying the amount of insulin delivered to the user 120 and a time that the insulin was delivered. The previous insulin delivery data may also include data specifying the type of insulin infused.

The mobile device 110 may determine an insulin delivery amount based on the previous insulin delivery data and the estimated glucose data without using recently entered user-specific data manually entered by the user 120. The insulin delivery amount may be sent from the mobile device 110 to the insulin pump 115 via a wireless communication channel.

In some embodiments, data may be communicated between the CGM 105 and the mobile device 110 and/or the insulin pump 115 and the mobile device 110 using the same or different wireless communication channels. These wireless channels, for example, may include any type of wireless channel such as, for example, Bluetooth, Bluetooth LE, Wi-Fi, WiMax, 4G, 5G, cellular, 433/868/915 MHz channels, etc. Each respective device may include one or more wireless transceivers (or radio and/or antenna) corresponding to the respective wireless channel such as for example, a Bluetooth transceiver, a Bluetooth LE transceiver, a Wi-Fi transceiver, a WiMax transceiver, 4G transceiver, 5G transceiver, 13 MHz transceiver, etc.

Figure 3:
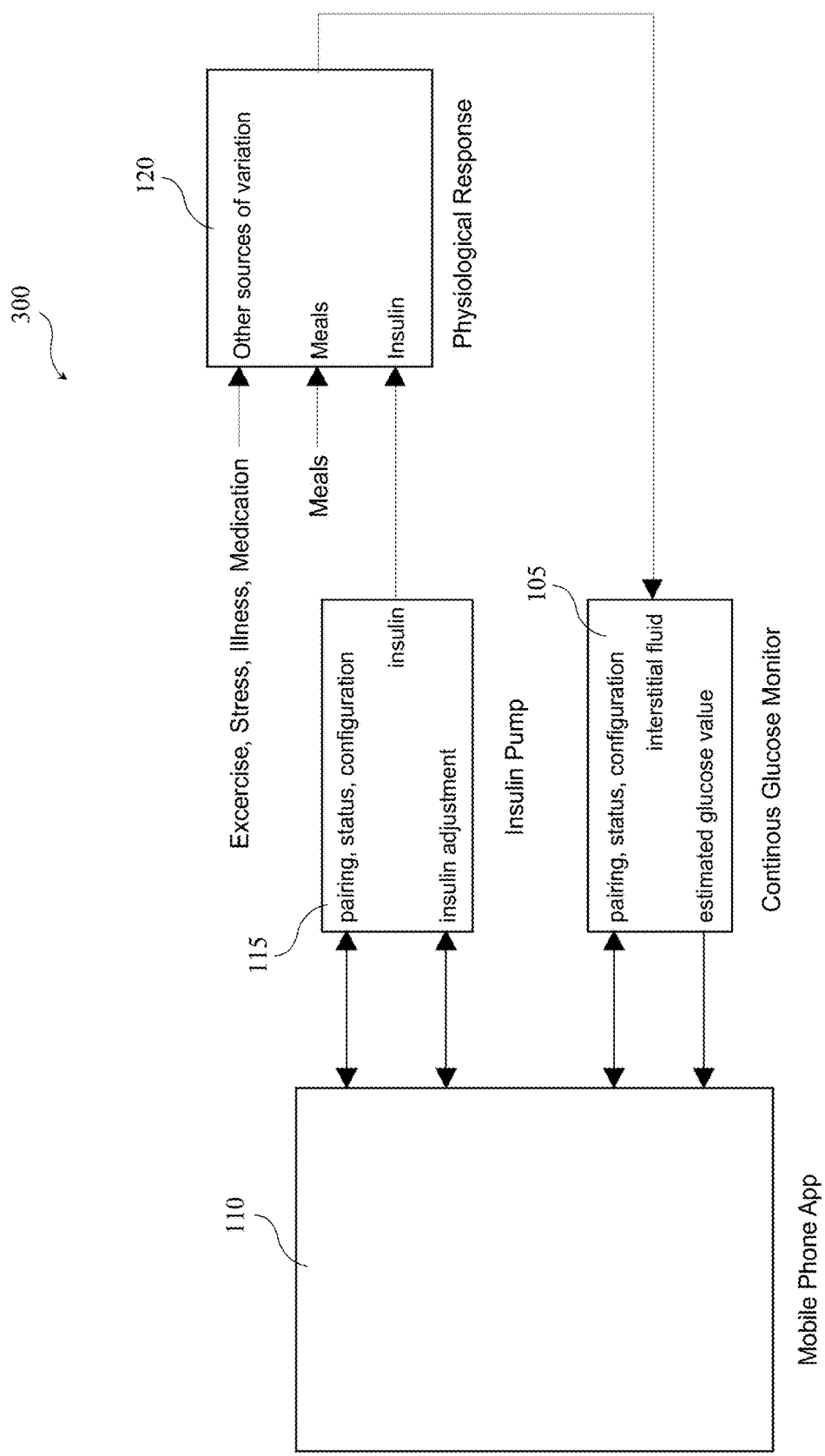
FIG. 3 is a functional block diagram of a glucose management system according to some embodiments.

FIG. 3 is a functional block diagram 300 of a glucose management system according to some embodiments. The block diagram 300 shows a representation of the user 120, the mobile device 110, the insulin pump 115, and the CGM 105. The block diagram 300 shows user inputs as meals and other inputs. The other inputs, for example, may include user-specific physiological data or user-specific behavioral data such as, for example, illness, stress, exercise, intimacy, medication, sleep, etc. These inputs represent behaviors that have an effect on the user's glucose levels and/or insulin needs.

The block diagram 300 shows the insulin pump 115 providing insulin delivery data to the mobile device 110. The insulin pump 115 may also provide wireless network pairing data, status information, configuration information, etc. to the mobile device 110.

In some embodiments, the insulin pump 115 may receive insulin delivery amounts from the mobile device 110, and/or pump insulin to the user 120 such as, for example, based on the provided insulin delivery amounts.

The block diagram shows the CGM 105 providing estimated glucose data to the mobile device 110. The CGM 105 may also provide wireless network pairing data, status information, configuration information, etc. to the mobile device 110. The CGM 105, for example, may determine estimated glucose data based on interstitial fluid received from the user 120. The CGM 105, for example, may determine estimated glucose data based on other factors.

The mobile device 110 may receive insulin delivery data from the insulin pump 115 and estimated glucose data from the CGM 105 and calculate an insulin delivery amount to the insulin pump 115.

Figure 4:
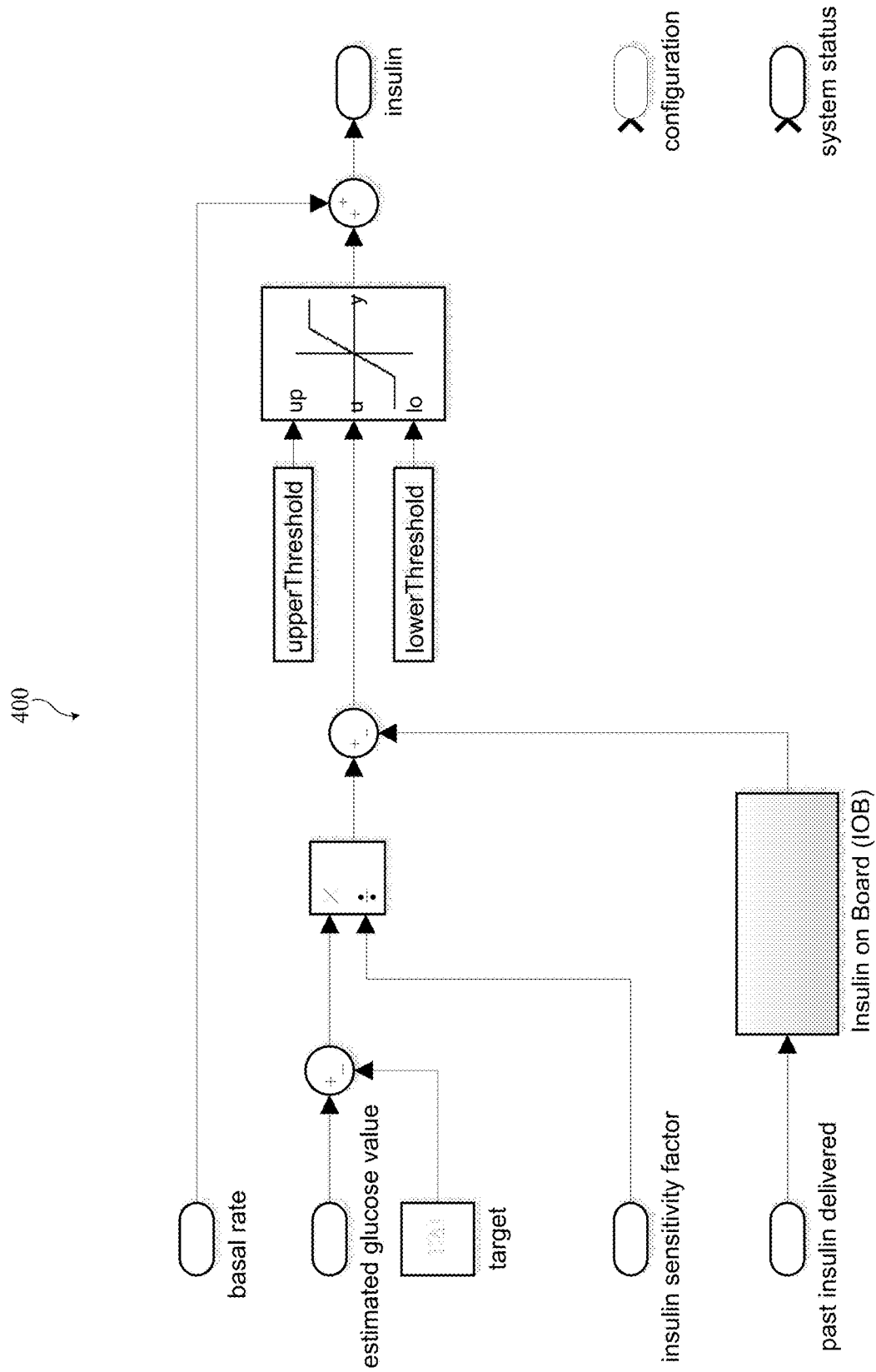
FIG. 4 is a flowchart of an algorithm that may be used in a glucose management system according to some embodiments.

FIG. 4 is a flowchart of an algorithm 400 that may be used in a glucose management system to determine the insulin delivery amount according to some embodiments.

In this example, an insulin delivery amount 405 is determined based on a basal insulin rate 410, estimated glucose value 415, and past insulin delivery data 420. The basal rate 410 may be the base insulin delivery rate (e.g., the amount and timing of insulin delivery) of the insulin pump 115. The basal rate 410 can also represent the amount of insulin required between the user's physiological or behavioral changes. Past insulin delivery data 420, for example, may be used to calculate an insulin on board value 430 which may represent the amount of insulin from a recent insulin delivery that is still working in the body. The difference between estimated glucose value 415 and a target glucose value 425 may be combined with an insulin sensitivity factor 440. The result may be a difference between the estimated glucose value 415 and a target glucose value 425.

This difference may be combined with the insulin on board value 430. The resulting value can be input into a function 435 that ensures the value remains between an upper and a lower threshold. This value may then combine with the basal rate 410. The resulting value may be the insulin delivery amount 405 that may be sent to the insulin pump. As noted, the insulin delivery amount 405 may be determined without using input user-specific physiological data and/or user-specific behavioral data.

Various other techniques, processes, equations, algorithms, etc. may be used to determine an insulin delivery amount 405.

Figure 5:
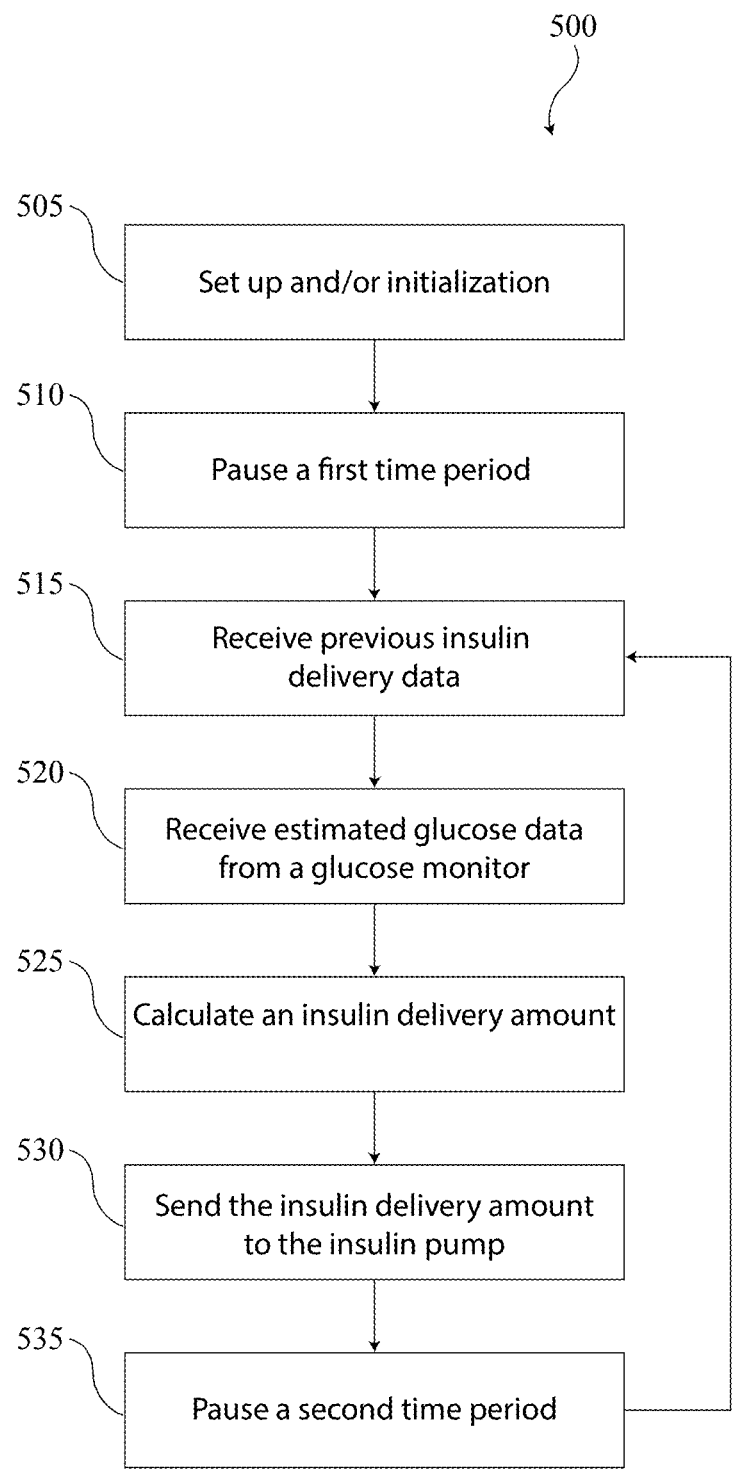
FIG. 5 is a flowchart of a process that may be used in a glucose management system according to some embodiments.

FIG. 5 is a flowchart of a process 500 that may be used in a glucose management system according to some embodiments. In some embodiments, the process 500 may include additional blocks. In some embodiments, the blocks in process 500 may be rearranged and/or may occur in any order; and additional blocks may be added. In some embodiments, one or more blocks in process 500 may be removed or replaced or skipped.

The process 500 may be executed by the mobile device 110 or the insulin pump 115.

The process 500 may begin at block 505 where the system may be set up and/or initialized. For example, at block 505 one or more initial parameters may be input by a user to initially set up the process or system. The initial parameter(s) may include, for example, the user's current total daily insulin use, the user's body weight, an insulin pump basal rate or basal profile, the user's current daily amount of long acting (basal) insulin or other insulin, user-specific physiological data, user-specific behavioral data, etc. The initial parameter(s) may include, for example, physiological data and/or behavioral data.

In some embodiments, the one or more initial parameters may be communicated to the mobile device 110.

In some embodiments, at block 505 the user's basal profile may be provided. The basal profile, for example, may be provided from the insulin pump 115 or manually entered by the user 120. The basal profile, for example, may indicate different basal rates for different times of the day. For example, the basal profile may indicate a constant rate over the day: 1 U/hr. As another example, the basal profile may be complex: midnight to 5 am 1 U/hr, 5 am to 8 am 1.2 U/hr, 8 am to 3 pm 1.1 U/hr, 3 pm to 10 pm 1.2 U/hr, and 10 pm to 5 am 1.1 U/hr. As another example, the basal profile may include a different profile for different days of the week. As another example, the basal rate may comprise a default insulin delivery rate. Any type of basal profile may be communicated.

At block 510, the process 500 may pause for a first time period. The first time period, for example, may allow the process 500 to initialize. The first time period, for example, may include any amount of time. As another example, the first time period may be a period of time from 0 minutes to 24 hours or more. As another example, the first time period may be an amount of time greater than 30, 60, 120, 240, 360, 480, etc. minutes.

At block 515 the mobile device 110 may receive medication delivery data. The medication delivery data, for example, may be received at the mobile device 110 from the insulin pump 115. The medication delivery data, for example, may include an amount of insulin delivered to the user over a period of time. The insulin delivery data, for example, may include the amount of insulin delivered over a set period of time such as, for example, 2 minutes, 5 minutes, 10 minutes, 15 minutes, etc.

In some embodiments, the medication delivery data may include information specifying the type of insulin delivered such as, for example, whether the delivered insulin was ultra-rapid acting insulin, rapid acting insulin, regular human insulin, concentrated insulins (e.g., U200, U400, U500), symlin coformulations, liver-responsive insulins, etc. In some embodiments, the medication delivery data may include information specifying the delivery method of the insulin such as, for example, inhalation, subcutaneous infusion, intraperitoneal, intravenous, etc.

In some embodiments, the medication delivery data may include an amount of medication (e.g., insulin, glucagon, hormones, conformations, other medications) delivered and a time the amount of medication was delivered. In some embodiments, the medication delivery data may include an average amount of medication in delivered of a period of time such as, for example, the period of time since the last medication delivery data was provided. In some embodiments, the medication delivery data may include a total amount of medication delivered of a period of time such as, for example, the period of time since the last medication delivery data was provided.

In some embodiments, the medication delivery data may include insulin delivery data such as, for example, an amount of insulin delivered over a period of time, an average amount of insulin delivered over a period of time, a total amount of insulin delivered over a period of time, an insulin amount and a time of delivery, etc.

In some embodiments, the medication delivery data may include glucagon delivery data such as, for example, an amount of glucagon delivered over a period of time, an average amount of glucagon delivered over a period of time, a total amount of glucagon delivered over a period of time, a glucagon amount and a time of delivery, etc.

In some embodiments, the medication delivery data may include hormone delivery data such as, for example, an amount of hormone delivered over a period of time, an average amount of hormone delivered over a period of time, a total amount of hormone delivered over a period of time, a hormone amount and a time of delivery, etc.

In some embodiments, the medication delivery data may include, for example, an amount of medication delivered over a period of time, an average amount of medication delivered over a period of time, a total amount of medication delivered over a period of time, a medication amount and a time of delivery, etc.

In some embodiments, the medication delivery data may be received at the mobile device 110 from the insulin pump 115 via a wireless communication channel.

In some embodiments, the mobile device 110 and the insulin pump 115 may be embedded as a single device and the insulin delivery data may be received by an integrated controller.

At block 520 the mobile device 110 may receive estimated glucose data. The estimated glucose data, for example, may include various data elements including a value specifying the estimated glucose value for the user 120. The estimated glucose value, for example, may include an estimated glucose value from a glucose sensor inserted on or under the user's skin 120. In some embodiments, the estimated glucose value may include an estimated blood glucose value derived or extrapolated from measurements from within the user's interstitial fluid. The estimated glucose value, for example, may include an estimated blood glucose value derived or extrapolated from measurements from the user's blood.

The estimated glucose data, for example, may be received at the mobile device 110 from the CGM 105. In some embodiments, the estimated glucose data may be received at the mobile device 110 from the CGM 105 via a wireless communication channel.

In some embodiments, the estimated glucose data may also include diagnostic data. The diagnostic data, for example, may include a noisy signal flag(s) that may indicate that the quality of the estimated glucose data may be suspect. In response, the process 500 may ignore the value sent with the noisy signal flag, interpolate, infer, predict, and/or extrapolate the estimated glucose data from a certain number of previous data points. The diagnostic data, for example, may include flags that may indicate non-physiologic events such as, for example, pressure-induced attenuation and/or a transient false low reading caused when pressure is applied to a CGM.

At block 525 an insulin delivery amount may be calculated from the estimated glucose data and the insulin delivery data without using any user-specific data that was physically entered by the user through the user interface of the mobile device within a previous period of time. The previous period of time, for example, may be the first time period of time. The user may, for example, have entered user-specific data via the user interface at any time prior to the previous period of time or the first period of time.

For example, the insulin delivery amount may be calculated from the estimated glucose data, the insulin delivery data and any data entered at block 505 such as, for example, any set up or initialization data.

As another example, the insulin delivery amount may be calculated from the estimated glucose data and the insulin delivery data without any additional user-specific data.

As another example, the insulin delivery amount may be calculated from the estimated glucose data and the insulin delivery data without any data manually or physically entered by the user into the mobile device 110.

As another example, the insulin delivery amount may be calculated from the estimated glucose data and the insulin delivery data with data from one or more other devices such as, for example, user-motion data from a watch, band, strap, patch, or other device worn, affixed, or implanted by the user, user-motion data from an accelerometer embedded within the mobile device 110 or the insulin pump 115, user-motion data from GPS device embedded within the mobile device 110 or the insulin pump 115, heart rate data from a heart rate monitor (e.g., a smart watch), sleep data from a device with a microphone or accelerometer, eating data from a watch having an accelerometer, ketone data from a ketone sensor, lactate data from a lactate sensor, hydration data from a hydration sensor, insulin data from an insulin sensor, etc.

As another example, the insulin delivery amount may be calculated from the estimated glucose data and the insulin delivery data using an algorithm similar to the algorithm shown in FIG. 4.

As another example, the insulin delivery amount may be calculated from the estimated glucose data and the insulin delivery data using a proportional integral derivative (PID) control algorithm. The PID control algorithm, for example, may calculate the insulin delivery amount based on a difference between the estimated glucose data and a target glucose amount, and/or a derivative of the estimated glucose data, and/or an integral of the estimated glucose data.

As another example, the insulin delivery amount may be calculated using model predictive control (MPC) such as, for example, nonlinear MPC, robust MPC, linear MPC, explicit MPC, etc.

As another example, the insulin delivery amount may be calculated using a linear-quadratic regulator (LQR) such as, for example, a Finite-horizon, continuous-time LQR, Infinite-horizon, continuous-time LQR, Finite-horizon, discrete-time LQR, Infinite-horizon, discrete-time LQR, etc.

As another example, the insulin delivery amount may be calculated using fuzzy logic control techniques.

As another example, the configuration (e.g., tuning, individualization, etc.) of the control algorithm (e.g. PID, LQR, MPC, fuzzy logic) may be calculated, revised, or adjusted from the estimated glucose data and the insulin delivery data using the Internal Model Control (IMC), Cohen-Coon, or Ziegler-Nichols tuning methods.

As another example, the insulin delivery amount may be calculated from the following equation:

$$\text{Insulin} = \max(\text{lower\_threshold}, \min(\text{upper\_threshold}, (\text{EGV}-\text{target})/\text{ISF}-\text{IOB}))$$

where EGV represents the estimated glucose value amount (e.g., from the estimated glucose data), ISF represents the insulin sensitivity factor, and IOB ("insulin on board") represents the amount of insulin from a recent insulin delivery that is still working in the body.

At block 535 the process 500 may pause for a second time period. The second time period, for example, may be less than the first time period. The second time period, for example, may be 1, 5, 10, 15, 30, etc. minutes.

Following block 530, the process 500 returns to block 515 and portions of the process 500 are repeated.

The process 500 describes, for example, a process for determining an insulin delivery amount and sending the insulin delivery amount to an insulin pump. The process 500 may also be used for delivering hormones or medication instead of or in addition to insulin.

In some embodiments, the process 500 may result in insulin delivery to a user without any alarms or notifications.

In some embodiments, the process 500 may manage glucose in a user without displaying or presenting values, trends, alerts, alarms, or patterns of physiological parameters or behavioral parameters a user such as, for example, on the display of a mobile device. These parameters may include, for example, estimated glucose values from a continuous glucose monitor, insulin delivery values from an insulin pump, bolus data, insulin delivery rates, insulin on board values, etc. The trends may include, for example, rates of changes of values, values relative to thresholds, etc. In some embodiments, these parameters may include the milligrams per deciliter (mg/dL) of glucose in the user's blood.

Trends, for example, may indicate that glucose levels are rising, rising sharply, rising slowly, remaining steady, decreasing quickly, decreasing slowly, etc. Trends may be represented, for example, with arrows showing magnitude, angle, and/or direction of the trend. Trends may be represented by logos, graphics, or charts. Trends may occur over a specific period of time (e.g., less than 6 hours) or include predictive trends.

In some embodiments, the process 500 may manage glucose in a user without alerting a user or triggering an alarm via a mobile device based on various triggers, thresholds, or trends unless, for example, the user's health is in danger such as, for example, in response to system data rather than physiological data or behavioral data. For example, rather than alert the user that glucose levels are reaching a threshold and possibly burden the user, the burden-free glucose management system may determine an insulin delivery amount that can nudge the glucose trend toward the threshold without any alerts, alarms, indications, trends, etc.

In some prior art processes or systems, these alerts or alarms might include an audible alarm or a vibration from a device.

Typically, in prior art processes or systems, for example, alarms or alerts may be set at various levels of glucose in the blood such as, for example, when the glucose levels fall below 55 mg/dL, 70 mg/dL, 85 mg/dL, etc. As another example from the prior art, alarms or alerts may be set at various levels of glucose in the blood such as, for example, when the glucose rise above 180 mg/dL, 200 mg/dL, 250 mg/dL, 300 mg/dL, 350 mg/dL, etc.

In some embodiments, rather than alert, alarm, provide an indication, or display data with a mobile device, data (e.g., glucose levels, estimated glucose levels, insulin on board values, insulin delivery data, etc.) may be communicated to a cloud monitoring service where the data may be monitored. If the user's health is at risk, the cloud service may communicate with the user as needed and/or possibly in a non-burdensome manner.

Figure 7:
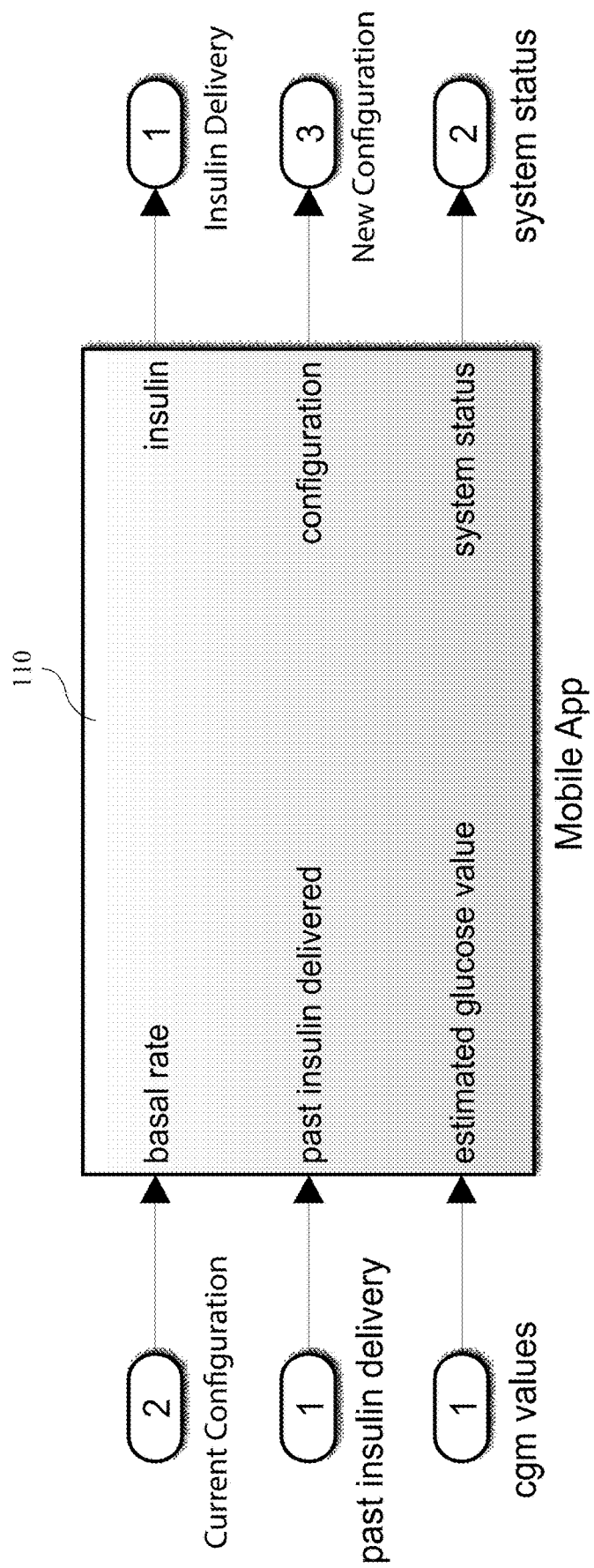
FIG. 7 is a block diagram showing the inputs and the outputs of a mobile device according to some embodiments.

FIG. 7 shows a block diagram of some of the inputs and outputs of a mobile device 110 according to some embodiments. The mobile device 110 may receive input regarding current configuration data, past insulin delivery data (e.g., from an insulin pump), and/or estimated glucose values (e.g., from a CGM). In some embodiments, the mobile device 110 running a mobile application may transmit insulin delivery values, configuration data, and/or system status data.

Figure 6:
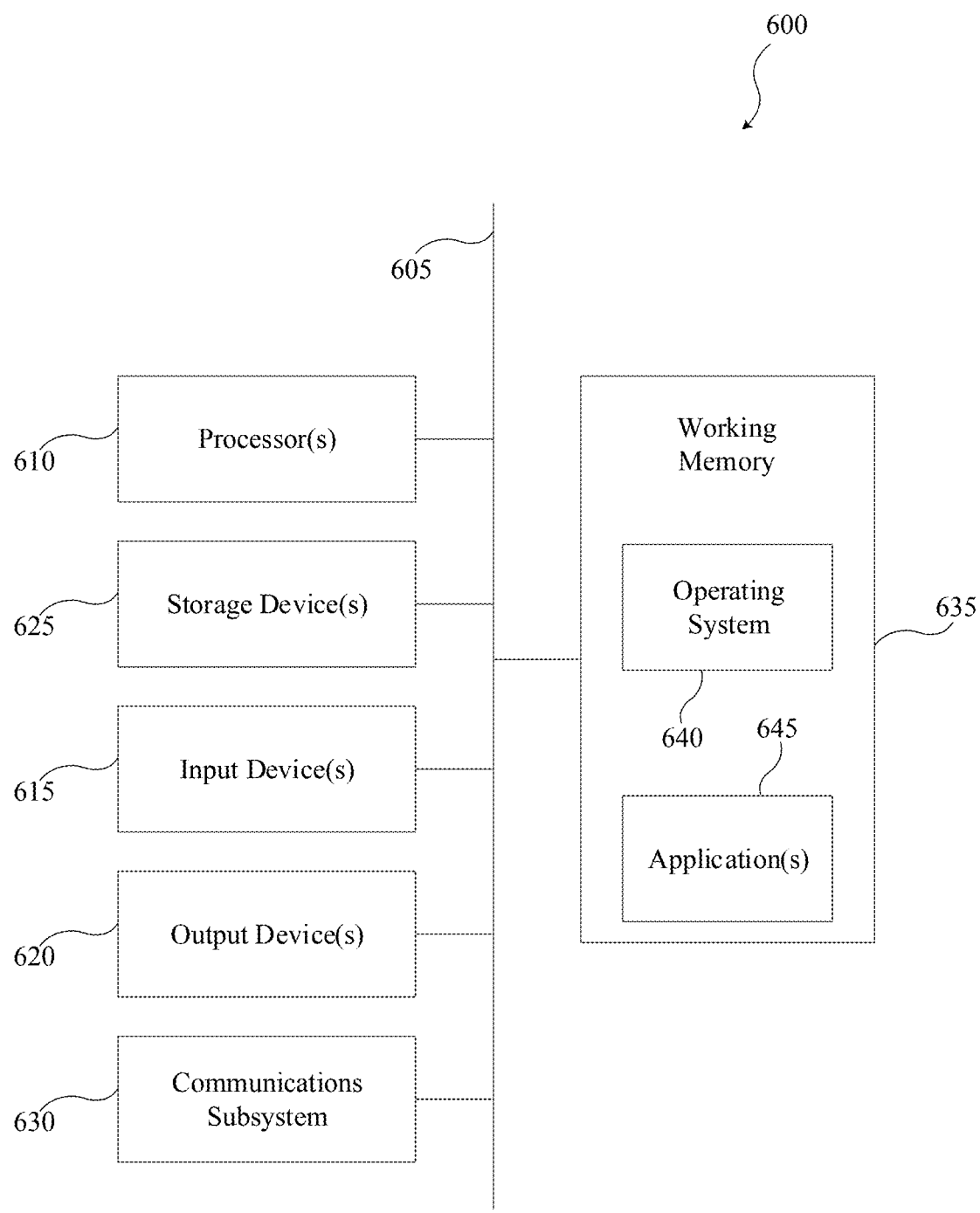
FIG. 6 shows an illustrative computational system for performing functionality to facilitate implementation of embodiments described in this document.

The computational system 600, shown in FIG. 6 can be used to perform any of the embodiments of the invention. For example, computational system 600 can be used to execute algorithm 400 and/or process 500. As another example, computational system 600 can be used to perform any calculation, identification and/or determination described here. Computational system 600 includes hardware elements that can be electrically coupled via a bus 605 (or may otherwise be in communication, as appropriate). The hardware elements can include one or more processors 610, including without limitation one or more general-purpose processors and/or one or more special-purpose processors (such as digital signal processing chips, graphics acceleration chips, and/or the like); one or more input devices 615, which can include without limitation a mouse, a keyboard, a touchscreen, a button and/or the like; and one or more output devices 620, which can include without limitation a display device, a printer and/or the like.

The computational system 600 may further include (and/or be in communication with) one or more storage devices 625, which can include, without limitation, local and/or network accessible storage and/or can include, without limitation, a disk drive, a drive array, an optical storage device, a solid-state storage device, such as a random access memory ("RAM") and/or a read-only memory ("ROM"), which can be programmable, flash-updateable and/or the like. The computational system 600 might also include a communications subsystem 630, which can include without limitation a modem, a network card (wireless or wired), an infrared communication device, a wireless communication device and/or chipset (such as a Bluetooth device, an 802.6 device, a Wi-Fi device, a WiMax device, cellular communication facilities, etc.), and/or the like. The communications subsystem 630 may permit data to be exchanged with a network (such as the network described below, to name one example), and/or any other devices described herein. In many embodiments, the computational system 600 will further include a working memory 635, which can include a RAM or ROM device, as described above.

The computational system 600 also can include software elements, shown as being currently located within the working memory 635, including an operating system 640 and/or other code, such as one or more application programs 645, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 625 described above.

In some cases, the storage medium might be incorporated within the computational system 600 or in communication with the computational system 600. In other embodiments, the storage medium might be separate from a computational system 600 (e.g., a removable medium, such as a compact disc, etc.), and/or provided in an installation package, such that the storage medium can be used to program a general-purpose computer with the instructions/code stored thereon. These instructions might take the form of executable code, which is executable by the computational system 600 and/or might take the form of source and/or installable code, which, upon compilation and/or installation on the computational system 600 (e.g., using any of a variety of generally available compilers, installation programs, compression/decompression utilities, etc.) then takes the form of executable code.

Unless otherwise specified, the term "substantially" means within 5% or 10% of the value referred to or within manufacturing tolerances. Unless otherwise specified, the term "about" means within 5% or 10% of the value referred to or within manufacturing tolerances.

The conjunction "or" is inclusive.

Numerous specific details are set forth herein to provide a thorough understanding of the claimed subject matter. However, those skilled in the art will understand that the claimed subject matter may be practiced without these specific details. In other instances, methods, apparatuses or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

That which is claimed:

1. A method comprising:
receiving previous insulin delivery data at a user device from an insulin pump;
receiving at the user device estimated glucose data from a continuous glucose monitor;
determining by the user device an insulin delivery amount based on 1) the previous insulin delivery data, 2) the estimated glucose data, and 3) user-specific behavioral data physically entered by a user through a user interface of the user device before expiration of a previous period of time to bring the estimated glucose data closer to a target glucose value, the previous period of time being three hours; and
communicating the insulin delivery amount from the user device to the insulin pump.

2. The method according to claim 1, wherein the previous insulin delivery data includes the amount of insulin delivered to the user over a period of time.

3. The method according to claim 1, wherein the insulin delivery data is received from the insulin pump via Bluetooth and/or the estimated glucose data is received from the continuous glucose monitor via Bluetooth.

4. The method according to claim 1, wherein the user-specific behavioral data comprises data selected from the list consisting of one or more of a mealtime announcement, a meal carbohydrate content estimate, an exercise announcement, and a sleep announcement.

5. The method according to claim 1, wherein the insulin delivery amount comprises an insulin correction to a basal insulin rate.

6. The method according to claim 1, wherein the user device and the insulin pump comprise a single device.

7. A glucose management system comprising:
a glucose monitoring device;
an insulin pump;
a user interface; and
a controller in communication with the glucose monitoring device, the insulin pump, and the user interface, the controller receives previous insulin delivery data from the insulin pump, the controller receives estimated glucose data from the glucose monitoring device, the controller determines an insulin delivery amount based on 1) the previous insulin delivery data, 2) the estimated glucose data, and 3) user-specific behavioral data physically entered by a user through a user interface of the user device before expiration of a previous period of time to bring an estimated glucose data closer to a target glucose value, the previous period of time being three hours, and the controller communicates the insulin delivery amount to the insulin pump.

8. The glucose management system according to claim 7, wherein the glucose monitoring device and the insulin pump communicate wirelessly with the controller.

9. The glucose management system according to claim 7, wherein the glucose monitoring device is a class II insulin pump and/or the glucose monitoring device is a class II integrated continuous glucose monitoring system.

10. The glucose management system according to claim 7, wherein the controller comprises a mobile device.

11. The glucose management system according to claim 7, wherein the controller and the insulin pump are part of a single device.

12. The glucose management system according to claim 7, wherein the user-specific data comprises either user-specific behavioral data or user specific physiological data.

13. The glucose management system according to claim 7, wherein the user-specific data comprises data selected from the list consisting of one or more of a mealtime announcement, a meal carbohydrate content estimate, an exercise announcement, a sleep announcement; a glucose value, an estimated glucose value, a ketone measurement, an insulin delivery trend, physical activity data, movement data, and exertion data.

14. The glucose management system according to claim 7,
wherein the controller wirelessly connects with either or both the glucose monitoring device or the insulin pump;
wherein the controller determines connectivity information regarding the connection between either or both the glucose monitoring device or the insulin pump; and
wherein the controller instructs the user interface to output connectivity information.

15. The glucose management system according to claim 7,
wherein the controller determines a fault in the glucose management system; and
wherein the controller instructs the user interface to output a fault indication;
wherein the fault comprises a fault selected from the list consisting of a glucose monitoring device end-of-life fault, a transient fault, a permanent fault, a battery end-of-life fault, a pump fault, an occlusion, a glucose sensor pull-out fault, a controller fault, and a system operation fault.

16. The glucose management system according to claim 7, wherein the insulin delivery amount comprises an insulin correction to a basal insulin rate.

17. A non-transitory computer-readable medium storing instructions that, when executed by a mobile computing device, cause the mobile computing device to:
receive previous insulin delivery data from an insulin pump;
receive estimated glucose data from a continuous glucose monitor;
determine an insulin delivery amount based on 1) the previous insulin delivery data, 2) the estimated glucose data, and 3) user-specific behavioral data physically entered by a user through a user interface of the user device before expiration of a previous period of time to bring the estimated glucose data closer to a target glucose value, the previous period of time being three hours; and
communicate the insulin delivery amount to the insulin pump.

18. The non-transitory computer-readable medium according to claim 17, wherein the user-specific data comprises either user-specific behavioral data or user specific physiological data.

19. The non-transitory computer-readable medium according to claim 17, wherein the user-specific data comprises data selected from the list consisting of one or more of a mealtime announcement, a meal carbohydrate content estimate, an exercise announcement, a sleep announcement; glucose value, an estimated glucose value, a ketone measurement, an insulin delivery trend, physical activity data, movement data, and exertion data.

20. The non-transitory computer-readable medium according to claim 17, wherein the insulin delivery amount comprises an insulin correction to a basal insulin rate.

* * * * *